(12) United States Patent
Hawkes et al.

(10) Patent No.: US 9,168,396 B2
(45) Date of Patent: Oct. 27, 2015

(54) COMPOSITION AND METHOD

(75) Inventors: Jamie Anthony Hawkes, Guiseley (GB); David Malcolm Lewis, Otley (GB); Céline Gauché, Hampshire (GB)

(73) Assignee: Perachem Limited, Yeadon, Leeds (GB)

( * ) Notice: Subject to any disclaimer, the term of this patent is extended or adjusted under 35 U.S.C. 154(b) by 396 days.

(21) Appl. No.: 13/575,115

(22) PCT Filed: Jan. 24, 2011

(86) PCT No.: PCT/GB2011/050114
§ 371 (c)(1),
(2), (4) Date: Jan. 14, 2013

(87) PCT Pub. No.: WO2011/092490
PCT Pub. Date: Aug. 4, 2011

(65) Prior Publication Data
US 2013/0133141 A1    May 30, 2013

(30) Foreign Application Priority Data

Jan. 26, 2010 (GB) .................................. 1001243.3

(51) Int. Cl.
*A61Q 9/04* (2006.01)
*A61K 8/19* (2006.01)
*A61K 8/22* (2006.01)
*A61K 8/362* (2006.01)
*A61K 8/368* (2006.01)
*A61K 8/40* (2006.01)

(52) U.S. Cl.
CPC ... *A61Q 9/04* (2013.01); *A61K 8/19* (2013.01); *A61K 8/22* (2013.01); *A61K 8/362* (2013.01); *A61K 8/368* (2013.01); *A61K 8/40* (2013.01); *A61K 2800/88* (2013.01); *A61K 2800/882* (2013.01)

(58) Field of Classification Search
CPC ....................................................... A61Q 9/04
USPC .............................................. 8/8, 161; 424/73
See application file for complete search history.

(56) References Cited

U.S. PATENT DOCUMENTS

| 2,371,875 | A | * | 3/1945 | Christopher | .................... 8/94.16 |
| 5,653,970 | A | * | 8/1997 | Vermeer | .................... 424/70.24 |
| 2004/0083557 | A1 | * | 5/2004 | Au et al. | .......................... 8/405 |

FOREIGN PATENT DOCUMENTS

| DE | 10 2006 021 006 A1 | 11/2007 |
| JP | 52 102439 A | 8/1977 |

OTHER PUBLICATIONS

XP-002686627 dated 1977.*
Stark, George R., "Reactions of Cyanate with Functional Groups of Proteins. III. Reactions with Amino and Carboxyl Groups", Biochemistry, American Chemical Society, 4(6): 1030-1036 (1965).
International Search Report and Written Opinion from corresponding International Application No. PCT/GB2011/050114, dated Nov. 19, 2012.

* cited by examiner

*Primary Examiner* — Eisa Elhilo
(74) *Attorney, Agent, or Firm* — Thomas H. Walls; Dann, Dorfman, Herrell and Skillman, P.C.

(57) ABSTRACT

A depilatory composition comprising a source of cyanate ion, an organic acid or a salt thereof and a peroxide compound; and methods of removing hair from the skin using such compositions.

12 Claims, No Drawings

COMPOSITION AND METHOD

The present invention relates to depilatory compositions and to methods and uses relating thereto. In particular the invention relates to the removal of human hair.

Hair removal has been practised for a variety of reasons over many centuries and there are many methods by which hair removal can be effected. One such method is chemical depilation in which a chemical is applied to weaken the hair allowing it to be removed more easily. Typically a chemical depilatory composition comprises a material which breaks down the disulfide bonds of keratin in the hair. Most current depilatory compositions are based on thioglycolic acids or salts thereof, for example calcium thioglycolate.

Depilatory compositions of the prior art typically work by reducing the disulfide bonds. However because they contain thioglycolate compounds, these compositions have an unpleasant smell. It is also necessary to use formulations which have a high pH in order for the thioglycolate-based active agent to be effective. The compositions are thus corrosive and can cause serious skin irritation, especially if used on a regular basis.

The present invention seeks to provide an alternative depilatory composition which does not contain a thioglycolic acid derived compound as the only depilatory agent.

According to a first aspect of the present invention there is provided a depilatory composition comprising a source of cyanate ion, an organic acid or a salt thereof and a peroxide compound.

The composition comprises a source of cyanate ion. This is suitably selected from an alkali metal cyanate, ammonium cyanate or a divalent metal cyanate. Preferred sources of cyanates are alkali metal and ammonium salts. Most preferred are potassium cyanate and especially sodium cyanate. Mixtures of two or more sources of cyanate ion may be present.

The cyanate ion is preferably present in the composition in an amount of at least 0.01 moldm$^{-3}$, preferably at least 0.1 moldm$^{-3}$, more preferably at least 0.2 moldm$^{-3}$, suitably at least 0.3 moldm$^{-3}$, for example at least 0.4 moldm$^{-3}$, preferably at least 0.5 moldm$^{-3}$, more preferably at least 0.6 moldm$^{-3}$.

The composition preferably comprises less than 10 moldm$^{-3}$ cyanate ion, preferably less than 5 moldm$^{-3}$, more preferably less than 3 moldm$^{-3}$, preferably less than 2 moldm$^{-3}$, suitably less than 1.2 moldm$^{-3}$, for example less than 1.0 moldm$^{-3}$.

In especially preferred embodiments the composition comprises 0.7 to 0.9 moldm$^{-3}$ cyanate ion.

The composition further comprises an organic acid or a salt thereof. Suitable organic acids include carboxylic acids, sulphonic acids and phosphorous containing acids. Thus suitable organic acids are compounds of formula RCOOH, RSO$_2$OH, RP(O)(OH)$_2$, RP(O)(OH)(OR) and R$_2$P(O)OH. Each R may be hydrogen or an optionally substituted alkyl, alkenyl, alkynyl or aryl group.

R may suitably be an alkyl or alkenyl group having 1 to 20 carbon atoms for example 1 to 15 carbon atoms, preferably 1 to 10 carbon atoms. The alkyl or alkenyl group may be optionally substituted with one or more substituents selected from hydroxy, alkoxy (for example methoxy), halo (for example chloro or bromo), alkyl (especially C$_1$ to C$_4$ alkyl, for example methyl), nitro, amino, mercapto, sulfoxy or COOH.

R may suitably be an optionally substituted aryl group having from 1 to 20 carbon atoms, preferably 1 to 15 carbon atoms, more preferably 1 to 10 carbon atoms. The aryl group may be a group containing only carbon atoms in the aromatic ring for example benzene or naphthalene or it may be a heteroaryl group comprising, in an aromatic ring, one or more heteroatoms selected from oxygen, nitrogen and sulphur. Preferred heteroaryl groups include those based on pyridine, pyrrole, pyrazole, imidazole, oxazole and thiophene. The aryl group may be optionally substituted with one or more substituents selected from hydroxy, alkoxy (for example methoxy), halo (for example chloro or bromo), alkyl (especially C$_1$ to C$_4$ alkyl, for example methyl), nitro, amino, mercapto, sulfoxy or COOH.

The organic acid is suitably selected from carboxylic acids, sulphonic acids and salts thereof.

Preferred sulfonic acids for use herein include 4-hydroxybenzene sulphonic acid, methane sulfonic acid and para-toluene sulfonic acid.

Preferably the organic acid comprises a carboxylic acid. The carboxylic acid may be a monocarboxylic acid, a dicarboxylic acid or a polycarboxylic acid. The carboxylic acid may be an aliphatic carboxylic acid or an aromatic carboxylic acid. Preferably the composition comprises a carboxylic organic acid having from 1 to 20 carbon atoms, suitably 1 to 15 carbon atoms, preferably 1 to 12 carbon atoms, more preferably 1 to 10 carbon atoms.

Suitable carboxylic acids include formic acid, acetic acid, propanoic acid, butanoic acid, pentanoic acid, hexanoic acid, heptanoic acid, octanoic acid, oxalic acid, malonic acid, succinic acid, glutaric acid, adipic acid, pimelic acid, suberic acid, azelic acid, sebacic acid, benzoic acid, toluic acid, phthalic acid, isophthalic acid, terephthalic acid, maleic acid, fumaric acid, nicotinic acid, stearic acid, lactic acid, citric acid and pivalic acid.

Preferably the carboxylic acid is selected from dicarboxylic acids and carboxylic acids including an aromatic group.

Preferred dicarboxylic acids include aliphatic (especially alkyl or alkenyl) and aromatic dicarboxylic acids, for example maleic acid, succinic acid and phthalic acid.

Preferred aromatic carboxylic acids include monocarboxylic acids and dicarboxylic acids, for example phthalic acid and benzoic acid.

The composition may comprise two or more organic acids.

Most preferably the organic acid is selected from maleic acid, succinic acid, phthalic acid, benzoic acid and mixtures thereof.

The organic acid may be present in the composition as the free acid or a salt thereof. Preferred salts are alkali metal and ammonium salts, for example sodium and potassium salts.

Preferably the organic acid or salt thereof is present in an amount of at least 0.01 moldm$^{-3}$, preferably at least 0.05 moldm$^{-3}$, more preferably at least 0.1 moldm$^{-3}$, preferably at least 0.2 moldm$^{-3}$, most preferably at least 0.3 moldm$^{-3}$, suitably at least 0.4 moldm$^{-3}$, for example at least 0.5 moldm$^{-3}$.

The organic acid or salt thereof may be present in an amount of up to 10 moldm$^{-3}$, preferably up to 5 moldm$^{-3}$, for example up to 2 moldm$^{-3}$, preferably up to 1.5 moldm$^{-3}$, more preferably up to 1.2 moldm$^{-3}$, suitably in an amount of up to 1.0 moldm$^{-3}$, for example in an amount of up to 0.9 moldm$^{-3}$.

In some preferred embodiments the organic acid or salt thereof is present in an amount of from 0.6 to 0.8 moldm$^{-3}$. In embodiments in which a mixture of carboxylic acids is present the above amounts refer to the total amount of all carboxylic acids in the composition.

The peroxide compound may be selected from any source of peroxide known to those skilled in the art. Preferably it is selected from hydrogen peroxide or a hydroperoxide of formula R'OOH wherein R' is a C$_1$ to C$_4$ alkyl group.

Alternatively the peroxide compound may comprise a solid peroxide source which releases hydrogen peroxide on contact with water. Such solid peroxide sources include perborates and percarbonates.

Most preferably the peroxide compound is hydrogen peroxide. Preferably this is provided as an aqueous solution of hydrogen peroxide.

In some embodiments hydrogen peroxide may be present in the composition as the perhydroxy anion.

Suitably the peroxide compound is present in an amount sufficient to provide the active hydrogen peroxide or the perhydroxy anion at a concentration of at least 0.01 moldm$^{-3}$, more preferably at least 0.05 moldm$^{-3}$, for example at least 0.1 moldm$^{-3}$, preferably at least 0.5 moldm$^{-3}$, more preferably at least 0.7 moldm$^{-3}$, for example at least 0.9 moldm$^{-3}$.

It may be present in an amount of up to 10 moldm$^{-3}$, for example up to 5 moldm$^{-3}$, preferably up to 3 moldm$^{-3}$ and more preferably up to 2 moldm$^{-3}$. It is suitably present in an amount of up to 1.5 moldm$^{-3}$, for example up to 1.3 moldm$^{-3}$.

Suitably the peroxide compound is present in an amount sufficient to provide the active hydrogen peroxide or perhydroxy at a concentration of 1 to 1.25 moldm$^{-3}$.

The above amounts refer to the amount of cyanate ion source, organic acid or salt thereof and peroxide compound added to the composition. The skilled person will appreciate that once formulated this mixture of components may undergo one or more chemical reactions. These chemical reactions may lead to the formation of the active depilatory in situ. More than one active depilatory species may be present.

Suitably the composition is an aqueous composition. Preferably it comprises at least 10 wt % water, preferably at least 20 wt % water, more preferably at least 50 wt % water, preferably at least 70 wt % water.

The composition may comprise a further solvent or diluent. Suitable solvents and diluents may be selected from those specified for cosmetic use by the Scientific Committee on Consumer Products (SCCP) managed by the Directorate General for Health and Consumer Protection of the European Commission. The SCCP approve a list of chemicals for use which is referred to as the INCI List (International Nomenclature of Cosmetic Ingredients List).

Preferred solvents and diluents include water, ethanol, isopropanol, n-propanol, butanol, propylene glycol, ethylene glycol, monoethyl ether, and mixtures thereof. Other suitable solvents are provided on the INCI list.

In some preferred embodiments the composition comprises a surfactant. This is suitably present in an amount of from 0.001 to 25 wt %, preferably from 0.01 to 20 wt %, more preferably from 0.05 to 15 wt %, for example from 0.1 to 10 wt %.

Suitable surfactants include anionic surfactants, cationic surfactants, non-ionic surfactants and zwitterionic surfactants. Zwitterionic surfactants are particularly preferred and most preferred are betaines, for example lauramidopropylbetaine. Other suitable surfactants include those listed on the INCI List. Suitable non-allergic surfactants are known to those skilled in the art.

The composition may comprise one or more thickeners. Preferred thickeners include those provided on the INCI List. Examples of such thickeners include oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22®, steareth-20 methacrylate copolymer; Aculyn 44 ®, polyurethane resin and Acusol 830 ®, acrylates copolymer which are available from Rohm and Haas, Philadelphia, Pa., USA. Additional thickening agents suitable for use herein include sodium alginate or gum arabic, or cellulose derivatives, such as methyl cellulose, hydroxyethyl cellulose or the sodium salt of carboxymethylcellulose or some types of acrylic polymers. Thickeners which undergo a change in viscosity with changing pH may be used. Examples of such thickeners are known to those skilled in the art.

The composition may comprise one or more further depilatory compounds. For example, it may comprise a thioglycolic acid derived compound, for example calcium thioglycolate. However in preferred embodiments the composition used in the method of the present invention is substantially free of thioglycolic acid derived compounds such as thioglycolate salts. Suitably it comprises less than 1 wt %, preferably less than 0.1 wt %, for example less than 0.01 wt % of thioglycolic acid derived compounds.

The composition may further comprise one or more optional excipients selected from fragrances, stabilisers, antimicrobials, conditioners, emulsion stabilisers, film formers, emulsifiers, antioxidants, chelators, antistatic agents, anti-caking agents, buffers, bulking agents, UV absorbers, moisturising agents, opacifiers, masking agents, reducing agents, humectants, foaming agents. Each of these components may be selected from the INCI list.

The composition suitably has a pH of from 2 to 10, preferably from 3 to 9, preferably from 4 to 8, more preferably 5 to 7.

This is lower than the pH of depilatory compositions of the prior art and this is less corrosive to the skin. Indeed, especially preferred compositions of the present invention have a pH of 5.5 to 6.5 which closely matches the natural pH of the skin.

Preferably the depilatory composition comprises a pH control agent. Any suitable acid or base may be used. Preferred pH control agents for use herein include those detailed on the INCI list. Preferably the composition comprises a base. Suitable bases include amine bases for example triethylamine and 2-amino-2-methyl-1-propanol, ammonium hydroxide and inorganic bases for example alkali-metal carbonates and hydroxides. In some preferred embodiments the composition comprises an alkali metal hydroxide, for example sodium hydroxide, or especially potassium hydroxide.

The depilatory composition of the present invention is suitably sufficiently mild to enable it to be used on the face of a user. The provision of a depilatory composition which has the efficacy to remove tough male facial hair yet is mild enough to be used on the face is a significant advantage of the composition of the present invention.

Where the composition of the present invention is used for removing male facial hair, it preferably further comprises a conditioning agent, although a conditioning agent may also be present in other embodiments.

The composition may be provided in any suitable form. For example, it may be provided as a gel, cream, lotion, aerosol, paste, roll-on or powder.

Suitably it is provided in the form which can be readily spread onto the skin but which holds its shape and position on the skin after application.

As mentioned previously, once added the components of the composition of the first aspect may react to form an active depilatory species in situ. The exact nature of the active depilatory species is not fully understood but it is believed to include a peroxide bond. Such compounds may be unstable under some storage conditions and thus may deteriorate over time. It may therefore by advantageous to form the depilatory composition comprising the active depilatory species shortly before use.

According to a second aspect of the present invention there is provided a depilatory product comprising a precursor composition which can be activated to form a composition of the first aspect.

In some preferred embodiments the precursor composition is activated to form a composition of the first aspect by admixture with one or more further compositions.

The depilatory product may comprise two precursor compositions for admixture immediately prior to application.

The depilatory product of the second aspect may comprise a first precursor composition comprising an organic acid or a salt thereof and a source of cyanate ion and a second precursor composition comprising a peroxide compound.

The peroxide compound is suitably selected from hydrogen peroxide or a compound which may be activated to provide hydrogen peroxide or the perhydroxy anion.

Preferred cyanate ion sources, organic acids and peroxide compounds are as defined in relation to the first aspect.

In some preferred embodiments the first precursor composition comprises one or more alkali metal cyanate salts and an organic acid or salt thereof. In some preferred embodiments the second precursor composition comprises hydrogen peroxide.

Further ingredients previously mentioned herein in relation to the first aspect may be provided in either or each of the first and second precursor compositions. The first and second precursor compositions may be liquid compositions which undergo a change in viscosity upon admixture.

Preferably any such change in viscosity is due to a change in pH upon admixture of the compositions.

In some alternative embodiments the depilatory product may comprise a single precursor composition which may be activated to form an activated depilatory composition. Such a precursor composition may comprise for example, a stabilised peroxide compound which only reacts upon, for example, exposure to air agitation or application of a force, for example a shear force.

The first and/or second precursor compositions may be encapsulated so that the two do not react in the single precursor composition during storage. The composition may be such that when a shear force is applied, for example as the composition is expelled from the container (for example through a nozzle or aerosol delivery mechanism) the two precursor compositions are then able to mix to form the composition of the first aspect which contains the active depilatory agent.

The first and second precursor compositions may alternatively be held in separate phases of an emulsion. The emulsion may be induced to break down by application of a shear force during delivery of the composition to the skin thus forming the active depilatory agent in situ.

In an alternative embodiment, the depilatory product may comprise a solid composition comprising a solid cyanate, solid organic acid or salt thereof and a solid peroxide compound. The depilatory composition comprising an active depilatory agent may be generated prior to application of the composition to the skin by addition of a diluent.

Suitable diluents include any cosmetically acceptable diluent or carrier as described above. In such embodiments the depilatory product may comprise a separate liquid composition in addition to the solid composition; the liquid composition comprising a diluent or diluent mixture for addition to the solid composition prior to application to the skin.

In some especially preferred embodiments the depilatory product comprises a first solid precursor composition comprising one or more solid organic acids or salts thereof, one or more solid sources of cyanate ion compounds and a second liquid precursor composition comprising a peroxide compound, for example hydrogen peroxide.

As mentioned above, either of the first and/or second compositions may comprise one or more further excipients. Preferred thickeners for use in a solid composition include hydroxymethyl cellulose and hydroxyethyl cellulose.

In some embodiments the depilatory product may be provided in a bicompartment container in which the first precursor composition is held in a first compartment and the second precursor composition is held in a second compartment, of the same container. Preferably the bicompartment container is arranged to deliver the first and second precursor compositions to the same locus. This may be achieved by providing adjacent outlets from the first and second compartments. Alternatively, the first and second compartments may be arranged to deliver the first and second precursor compositions into a common passageway in which they are contacted prior to exiting the container through a single outlet. Bicompartment containers of this type are known to the person skilled in the art. One such example is a squeezable tube (known as a "dual tube") having two compartments comprising the two precursor compositions. Squeezing the tube causes the two compositions to be delivered through adjacent outlets such that they come into immediate contact with each other on exiting the container. Other embodiments of bicompartment containers also include bottles or canisters for holding mousses, gels or sprays which are provided with a single actuator which effects delivery of the two precursor compositions to the same locus via the same or adjacent outlets. Alternatively the depilatory product of the present invention may be provided as two discrete precursor compositions which are packaged separately in individual containers.

According to a third aspect of the present invention there is provided a method of removing hair from the skin, the method comprising the steps of:

a) contacting the skin with a composition of the first aspect; and b) removing said composition from the skin along with entrained hair.

Preferred aspects of the third aspect are as defined in relation to the first and second aspects.

In step (a) of the method of the third aspect the skin is contacted with the composition for a period sufficient to affect depilation of hair growing thereon. Preferably the skin is contacted with the composition for a period sufficient to effect removal of at least 5% of the hairs growing thereon, preferably at least 10%, more preferably at least 20%, for example at least 30%, preferably at least 40% and most preferably at least 50%. In especially preferred embodiments the composition may remove at least 60% of the hairs growing on the skin in the area treated with the composition, for example at least 70%, preferably at least 80% and most preferably at least 90%. In some embodiments substantially all of the hair, for example greater than 95%, may be removed by the method of the present invention.

Suitably step (a) comprises contacting the skin with the composition for a period of up to 2 hours, for example up to 90 minutes, preferably up to 60 minutes, for example up to 50 minutes, preferably up to 40 minutes.

Step (a) comprises contacting the composition with the skin for a period of at least 2 seconds, more preferably at least 5 seconds, for example at least 10 seconds, more preferably at least 30 seconds, for example at least 1 minute. It may comprise contacting the skin with the composition for at least 2 minutes or at least 3 minutes, for example at least 4 minutes.

The composition applied to the skin may have a temperature of from 0 to 50° C., for example 5 to 45° C., or from 10 to 30° C. It may suitably be applied at ambient temperature.

A particular advantage of preferred compositions of the present invention is that they have been found to provide effective hair removal after short application periods, for example less than 10 minutes, but they do not cause significant skin irritation if left in contact with the skin for longer periods, for example up to 30 minutes.

In step (b) the composition and entrained hair may be removed from the skin by any suitable means. It may for example be simply rinsed away with water, or it may be scraped off, for example using a spatula. It may be rubbed off using the hands or it may be wiped clean with a cloth.

It is believed that in the method of the present invention the depilatory action is achieved by oxidative cleavage of the cystine disulfide bonds of the keratin in the hair. This involves a very different mechanism to compositions of the prior art in which disulfide bonds are reduced. The active depilatory species formed in the present invention is believed to be an oxidant. Preferably the composition is substantially free of reducing agents.

In some embodiments the method of the present invention may be a method of removing facial hair. This may be used by men instead of shaving.

In embodiments in which the composition of the first aspect is provided as a depilatory product of the second aspect the method of the third aspect may comprise a step prior to step (a) of preparing the composition of the first aspect by activating the precursor composition.

This step may suitably comprise admixing a first composition comprising a source of cyanate ion and an organic acid or salt thereof and a second composition comprising a peroxide compound.

According to a fourth aspect of the present invention there is provided a kit comprising a composition of the first aspect or a depilatory product of the second aspect, and instructions for hair removal.

Preferred aspects of the fourth aspect are as defined in relation to the first, second or third aspects as appropriate.

Where the kit of fourth aspect comprises the depilatory product of the second aspect, the kit of the fourth aspect may further comprise instructions for preparing the depilatory composition of the first aspect prior to application. The composition may suitably be prepared immediately prior to application. The depilatory composition of the first aspect comprising the active depilatory species may be prepared up to 12 hours prior to application, for example up to 8 hours, preferably up to 6 hours, preferably up to 4 hours, for example up to 2 hours, preferably up to 1 hour, for example up to 30 minutes and most preferably up to 10 minutes.

In embodiments in which the depilatory product comprises a solid composition which must be mixed with a diluent prior to admixture, the kit of the fourth aspect may further comprise instructions for preparing the active depilatory composition. It may optionally comprise a container and/or stirrer for assisting in the preparation of said active composition.

The kit of the fourth aspect may further comprise a tool for assisting hair removal. Such tools include for example a cloth or a plastic spatula and are well known to those skilled in the art.

The kit of the fourth aspect may further comprise a conditioning agent for application to the skin following hair removal. The conditioning agent may be provided in a lotion or impregnated on a wipe.

According to a fifth aspect of the present invention there is provided the use of a composition comprising a source of cyanate ion, an organic acid or a salt thereof and a peroxide compound to remove hair from skin.

The present invention will now be further described with reference to the following non-limiting examples.

EXAMPLE 1

A two-part depilatory composition was prepared having the following composition:

| Part 1 | | Part 2 | |
|---|---|---|---|
| 68% | Phthalic acid | 22% | KOH (25% w/w solution) |
| 32% | NaOCN | 78% | $H_2O_2$ (5.5% total peroxide) |

An active depilatory composition was prepared by mixing 5 g of Part 1 with 28.2 g of part 2. This gave a formulated composition comprising the following:

| 10.2% w/w | Phthalic acid |
|---|---|
| 4.8% w/w | NaOCN |
| 18.7% w/w | KOH (25% w/w solution) |
| 66.3% w/w | $H_2O_2$ (5.2% total peroxide) |

The composition was applied to the skin and left for 10 minutes before rinsing with warm water. On the area of skin thus treated substantially all of the hair had been removed and no skin irritation was observed.

EXAMPLE 2

A two-part depilatory composition was prepared having the following composition:

| Part 1 | | Part 2 | |
|---|---|---|---|
| 59.8% | Maleic acid | 22.8% | KOH (25% w/w solution) |
| 40.2% | NaOCN | 77.2% | $H_2O_2$ (5.2% total peroxide) |

An active depilatory composition was prepared by mixing 4 g of Part 1 with 29.8 g of part 2. This gave a formulated composition comprising the following:

| 7.0% w/w | Maleic acid |
|---|---|
| 4.7% w/w | NaOCN |
| 20.1% w/w | KOH (25% w/w solution) |
| 67.7% w/w | $H_2O_2$ (5.2% total peroxide) |

The composition was applied to the skin and left for 20 minutes before rinsing with warm water. On the area of skin thus treated substantially all of the hair had been removed and no skin irritation was observed.

EXAMPLE 3

A two-part depilatory composition was prepared having the following composition:

| Part 1 | | Part 2 | |
|---|---|---|---|
| 60.2% | Succinic acid | 20.5% | KOH (25% w/w solution) |
| 39.8% | NaOCN | 79.5% | $H_2O_2$ (5.0% total peroxide) |

An active depilatory composition was prepared by mixing 4 g of Part 1 with 30.1 g of part 2. This gave a formulated composition comprising the following:

| | |
|---|---|
| 7.1% w/w | Succinic acid |
| 4.7% w/w | NaOCN |
| 18.1 w/w | KOH (25% w/w solution) |
| 70.5% w/w | $H_2O_2$ (5.0% total peroxide) |

The composition was applied to the skin and left for 15 minutes before rinsing with warm water. On the area of skin thus treated substantially all of the hair had been removed and no skin irritation was observed.

EXAMPLE 4

A two-part depilatory composition was prepared having the following composition:

| Part 1 | | Part 2 | |
|---|---|---|---|
| 61.0% | Benzoic acid | 13.7% | KOH (25% w/w solution) |
| 39.0% | NaOCN | 86.3% | $H_2O_2$ (4.6% total peroxide) |

An active depilatory composition was prepared by mixing 4.1 g of Part 1 with 30.1 g of part 2. This gave a formulated composition comprising the following:

| | |
|---|---|
| 7.3% w/w | Benzoic acid |
| 4.7% w/w | NaOCN |
| 12.1 w/w | KOH (25% w/w solution) |
| 76.2% w/w | $H_2O_2$ (4.6% total peroxide) |

The composition was applied to the skin and left for 30 minutes before rinsing with warm water. On the area of skin thus treated substantially all of the hair had been removed and no skin irritation was observed.

EXAMPLE 5

A two-part depilatory composition was prepared having the following composition:

| Part 1 | | Part 2 | |
|---|---|---|---|
| 43.0% | Phthalic acid | 18% | KOH (25% w/w solution) |
| 20.3% | NaOCN | 82% | $H_2O_2$ (6% total peroxide) |
| 36.7% | Hydroxyethylcellulose | | |

An active depilatory composition was prepared by mixing 7.9 g of Part 1 with 24.4 g of part 2. This gave a formulated composition comprising the following:

| | |
|---|---|
| 10.5% w/w | Phthalic acid |
| 5.0% w/w | NaOCN |
| 13.6% w/w | KOH (25% w/w solution) |
| 61.9% w/w | $H_2O_2$ (6% total peroxide) |
| 9% w/w | Hydroxyethylcellulose |

The composition was applied to the skin and left for 10 minutes before rinsing with warm water. On the area of skin thus treated substantially all of the hair had been removed and no skin irritation was observed.

EXAMPLE 6

A two-part depilatory composition was prepared having the following composition:

| Part 1 | | Part 2 | |
|---|---|---|---|
| 40.2% | Succinic acid | 22.8% | KOH (25% w/w solution) |
| 26.6% | NaOCN | 77.2% | $H_2O_2$ (6.0% total peroxide) |
| 33.2% | Hydroxyethylcellulose | | |

An active depilatory composition was prepared by mixing 6 g of Part 1 with 26 g of part 2. This gave a formulated composition comprising the following:

| | |
|---|---|
| 7.6% w/w | Succinic acid |
| 5% w/w | NaOCN |
| 18.4% w/w | KOH (25% w/w solution) |
| 62.7% w/w | $H_2O_2$ (6% total peroxide) |
| 6.3% w/w | Hydroxyethycellulose |

The composition was applied to the skin and left for 15 minutes before rinsing with warm water. On the area of skin thus treated substantially all of the hair had been removed and no skin irritation was observed.

EXAMPLE 7

A two-part packaged depilatory product was prepared having the following composition:

| Depilatory Powder | | Depilatory Solution | |
|---|---|---|---|
| 3.4 g | Potassium biphthalate | 4.4 g | KOH (25% w/w solution) |
| 1.6 g | NaOCN | 10 g | $H_2O_2$ (12% by volume solution) |
| 2.9 g | Hydroxyethylcellulose | 10 g | Water |

Following the instructions supplied with the packaged depilatory product, the active depilatory composition was prepared by adding the depilatory powder to the depilatory solution. The mixture was stirred or shaken for 10 to 20 seconds to provide a cream. This cream was immediately applied to the skin to provide a good even coverage. After 5 minutes, the composition and entrained hair were removed using a scaper tool supplied with the packaged depilatory product. The skin was well rinsed with warm water. On the area of skin thus treated substantially all of the hair had been removed and no skin irritation was observed.

EXAMPLE 8

A two-part packaged depilatory product was prepared having the following composition:

| Depilatory Powder | | Depilatory Solution | |
|---|---|---|---|
| 3.4 g | Potassium biphthalate | 10 g | $H_2O_2$ (12% by volume solution) |
| 1.6 g | NaOCN | 13.3 g | Water |
| 2.9 g | Hydroxyethylcellulose | | |
| 1.1 g | KOH | | |

Following the instructions supplied with the packaged depilatory product, the active depilatory composition was prepared by adding the depilatory powder to the depilatory solution. The mixture was stirred or shaken for 10 to 20 seconds to provide a cream. This cream was immediately applied to the skin to provide a good even coverage. After 5 minutes, the composition and entrained hair were removed using a scaper tool supplied with the packaged depilatory product. The skin was well rinsed with warm water. On the area of skin thus treated substantially all of the hair had been removed and no skin irritation was observed.

The invention claimed is:

1. A depilatory composition for removal of human hair comprising a source of cyanate ion, an organic acid or a salt thereof and a peroxide compound; wherein the organic acid or salt thereof is at least one organic acid or salt thereof selected from dicarboxylic acids and carboxylic acids including an aromatic group; and wherein the composition has a pH of from 5 to 7.

2. A depilatory composition according to claim 1 wherein the source of cyanate ion is selected from potassium cyanate, sodium cyanate and mixtures thereof.

3. A depilatory composition according to claim 1 wherein the organic acid or salt thereof is at least one organic acid or salt thereof selected from maleic acid, succinic acid, phthalic acid, benzoic acid and mixtures and salts thereof.

4. A depilatory composition according to claim 1 wherein the peroxide compound comprises hydrogen peroxide.

5. A depilatory composition according to claim 1 comprising at least 70 wt % water.

6. A depilatory product comprising a precursor composition which can be activated to form the composition of claim 1.

7. A depilatory product according to claim 6 which comprises a first precursor composition comprising an organic acid or a salt thereof and a source of cyanate ion and a second precursor composition comprising a peroxide compound.

8. A method of removing human hair from skin, the method comprising the steps of:
   a) contacting the skin with the composition of claim 1; and
   b) removing said composition from the skin along with entrained hair.

9. A kit comprising the depilatory composition of claim 1; and instructions for use of said composition to effect hair removal.

10. A kit according to claim 9 which further comprises a tool for assisting hair removal.

11. A method of removing human hair from skin comprising applying to skin from which hair is growing a composition according to claim 1 in an amount effective to remove hair.

12. A kit comprising the depilatory product of claim 6; and instructions for use of said product to effect hair removal.

* * * * *